United States Patent
Zhou et al.

(10) Patent No.: US 7,227,924 B2
(45) Date of Patent: Jun. 5, 2007

(54) COMPUTED TOMOGRAPHY SCANNING SYSTEM AND METHOD USING A FIELD EMISSION X-RAY SOURCE

(75) Inventors: Otto Z. Zhou, Chapel Hill, NC (US); Yuan Cheng, Chapel Hill, NC (US); Jian Zhang, Chapel Hill, NC (US); Yueh Lee, Durham, NC (US); Jianping Lu, Chapel Hill, NC (US); Weili Lin, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 11/051,332

(22) Filed: Feb. 7, 2005

(65) Prior Publication Data

US 2005/0226361 A1    Oct. 13, 2005

Related U.S. Application Data

(63) Continuation-in-part of application No. 10/051,183, filed on Jan. 22, 2002, now Pat. No. 6,876,724, which is a continuation-in-part of application No. 09/679,303, filed on Oct. 6, 2000, now Pat. No. 6,553,096.

(60) Provisional application No. 60/544,420, filed on Feb. 13, 2004.

(51) Int. Cl.
*G01N 23/00* (2006.01)

(52) U.S. Cl. .......................... 378/10; 378/20

(58) Field of Classification Search .................... 378/4, 378/122, 9, 10, 12, 20
See application file for complete search history.

(56) References Cited

U.S. PATENT DOCUMENTS 2,842,706 A    7/1958    Dobischek et al.
(Continued)

FOREIGN PATENT DOCUMENTS

DE    197 00 992    7/1998
(Continued)

OTHER PUBLICATIONS

Bower et al., "Fabrication and Field Emission Properties of Carbon Nanotube Cathodes", edited by Sullivan, J. Robertson, O. Zhou, T. Allen and B. Coll, *Mat. Res. Soc. Symp. Proc.*, vol. 593, pp. 215-220 (2000).
(Continued)

*Primary Examiner*—Edward J. Glick
*Assistant Examiner*—Hoon Song
(74) *Attorney, Agent, or Firm*—Jenkins, Wilson, Taylor & Hunt, P.A.

(57) ABSTRACT

Computed tomography scanning systems and methods using a field emission x-ray source are disclosed. An exemplary micro-computed tomography scanner comprises a micro-focus field emission x-ray source, an x-ray detector, an object stage placed between the x-ray source and the detector, an electronic control system and a computer that control the x-ray radiation and detector data collection, and computer software that reconstructs the three dimension image of the object using a series of projection images collected from different projection angles. Exemplary methods obtain a computed tomography image of an object in oscillatory motion using the micro computed tomography scanner.

26 Claims, 4 Drawing Sheets

U.S. PATENT DOCUMENTS

| | | | |
|---|---|---|---|
| 3,733,484 A | 5/1973 | Bayard | |
| 3,753,020 A | 8/1973 | Zingaro | |
| 3,783,288 A | 1/1974 | Barbour et al. | |
| 3,921,022 A | 11/1975 | Levine | |
| 4,012,656 A | 3/1977 | Norman et al. | |
| 4,253,221 A | 3/1981 | Cochran, Jr. et al. | |
| 4,289,969 A | 9/1981 | Cooperstein et al. | |
| 4,958,365 A | 9/1990 | Sohval et al. | |
| 5,129,850 A | 7/1992 | Kane et al. | |
| 5,138,237 A | 8/1992 | Kane et al. | |
| 5,305,363 A | 4/1994 | Burke et al. | |
| 5,371,778 A * | 12/1994 | Yanof et al. | 378/4 |
| 5,377,249 A | 12/1994 | Wiesent et al. | |
| 5,424,054 A | 6/1995 | Bethune et al. | |
| 5,616,368 A | 4/1997 | Jin et al. | |
| 5,623,180 A | 4/1997 | Jin et al. | |
| 5,637,950 A | 6/1997 | Jin et al. | |
| 5,648,699 A | 7/1997 | Jin et al. | |
| 5,726,524 A | 3/1998 | Debe | |
| 5,773,834 A | 6/1998 | Yamamoto et al. | |
| 5,773,921 A | 6/1998 | Keesmann et al. | |
| 5,844,963 A | 12/1998 | Koller et al. | |
| 5,910,974 A | 6/1999 | Kuhn et al. | |
| 5,973,444 A | 10/1999 | Xu et al. | |
| 5,976,444 A | 11/1999 | Pearson et al. | |
| 6,019,656 A | 2/2000 | Park et al. | |
| 6,057,637 A | 5/2000 | Zettl et al. | |
| 6,087,765 A | 7/2000 | Coll et al. | |
| 6,250,984 B1 | 6/2001 | Jin et al. | |
| 6,259,765 B1 | 7/2001 | Baptist | |
| 6,277,318 B1 | 8/2001 | Bower et al. | |
| 6,280,697 B1 | 8/2001 | Zhou et al. | |
| 6,297,592 B1 | 10/2001 | Goren et al. | |
| 6,333,968 B1 * | 12/2001 | Whitlock et al. | 378/136 |
| 6,334,939 B1 | 1/2002 | Zhou et al. | |
| 6,385,292 B1 | 5/2002 | Dunham et al. | |
| 6,440,761 B1 | 8/2002 | Choi | |
| 6,445,122 B1 | 9/2002 | Chuang et al. | |
| 6,456,691 B2 | 9/2002 | Takahashi et al. | |
| 6,459,767 B1 | 10/2002 | Boyer | |
| 6,470,068 B2 * | 10/2002 | Cheng | 378/20 |
| 6,498,349 B1 | 12/2002 | Thomas et al. | |
| 6,553,096 B1 | 4/2003 | Zhou et al. | |
| RE38,223 E | 8/2003 | Keesmann et al. | |
| 6,630,772 B1 | 10/2003 | Bower et al. | |
| 6,650,730 B2 | 11/2003 | Bogatu et al. | |
| 6,674,837 B1 | 1/2004 | Taskar et al. | |
| 6,760,407 B2 * | 7/2004 | Price et al. | 378/122 |
| 6,850,595 B2 | 2/2005 | Zhou et al. | |
| 6,852,973 B2 | 2/2005 | Suzuki et al. | |
| 6,876,724 B2 | 4/2005 | Zhou et al. | |
| 6,965,199 B2 | 11/2005 | Stoner et al. | |
| 2002/0085674 A1 | 7/2002 | Price et al. | |
| 2002/0110996 A1 | 8/2002 | Yaniv et al. | |
| 2002/0140336 A1 | 10/2002 | Stoner et al. | |
| 2002/0171357 A1 | 11/2002 | Sun et al. | |
| 2003/0002627 A1 | 1/2003 | Espinosa et al. | |
| 2003/0198318 A1 | 10/2003 | Price | |
| 2004/0028183 A1 | 2/2004 | Lu et al. | |
| 2004/0036402 A1 | 2/2004 | Keesmann et al. | |
| 2004/0114721 A1 | 6/2004 | Qiu et al. | |
| 2004/0240616 A1 | 12/2004 | Qiu et al. | |
| 2005/0175151 A1 * | 8/2005 | Dunham et al. | 378/122 |

FOREIGN PATENT DOCUMENTS

| | | |
|---|---|---|
| DE | 101 64 315 A1 | 8/2002 |
| WO | WO 00/51936 | 9/2000 |
| WO | WO 02/31857 | 4/2002 |
| WO | WO 03/012816 A2 | 2/2003 |

OTHER PUBLICATIONS

Saito et al., "Field Emission Patterns from Single-Walled Carbon Nanotubes", *Jpn. J. Appl. Phys.*, vol. 36 pp. L1340-L1342, Part 2, No. 10A, Oct. 1, 1997.

Saito et al., "Cathode Ray Tube Lighting Elements with Carbon Nanotube Field Emitters", *Jpn. J. Appl. Phys.*, vol. 37, pp. L346-L348., Part 2, No. 3B, Mar. 15, 1998.

Zhu et al., "Large Current Density from Carbon Nanotube Field Emitters", *Appl. Phys. Lett.*, American Institute of Physics, vol. 75, No. 6, Aug. 9, 1999, pp. 873-875.

Radiologic Science For Technologist, Physics, Biology, and Protection, 6th Edition, S.C. Bushong, Mosby, Inc., 1997 (excerpt relating to focusing and thermionic emission).

Zhu et al., "Low-Field Electron Emission from Undoped Nanostructured Diamond", *Science*, vol. 282, 1471-1473 (Nov. 20, 1998).

Brodie et al., "Vacuum Microelectronics", *Advances in Electronics and Electron Physics*, edited by P.W. Hawkes, vol. 83, pp. 1-106 (1992).

Okano et al., "Electron emission from nitrogen-doped pyramidal-shape diamond and its battery operation", *Appl. Phys. Lett.*, vol. 70, No. 16, pp. 2201-2203 (Apr. 21, 1997).

Okano et al., "Fabrication of a diamond field emitter array", *Appl. Phys. Lett.*, vol. 64, No. 20, pp. 2742-2744 (May 16, 1994).

Kumar et al., "Diamond-based field emission flat panel displays", *Solid State Technology*, vol. 38, pp. 71-74 (May 1995).

Geis et al., "Diamond emitters fabrication and theory," *J. Vac. Sci. Technol. B*, vol. 14, No. 3, pp. 2060-2067, May/Jun. 1996.

Rinzler et al., "Unraveling Nanotubes: Field Emission from an Atomic Wire," *Science*, vol. 269, pp. 1550-1553 (Sep. 15, 1995).

de Heer et al., "A Carbon Nanotube Field-Emission Electron Source," *Science*, vol. 270, pp. 1179-1180 (Nov. 17, 1995).

Okazaki et al., "A New Emission Spectrum of $Au_2$ in the Gas Evaporation Technique: 761-809 nm," *Jpn. J. Appl. Phys.*, vol. 37, Pt. 1, No. 1, pp. 349-350 (Jan. 1998).

Wang et al., "Field emission from nanotube bundle emitters at low fields," *Appl. Phys. Lett.*, vol. 70, No. 24, pp. 3308-3310 (Jun. 16, 1997).

Yagishita et al., "Effects of Cleavage on Local Cross-Sectional Stress Distribution in Trench Isolation Structure", *Jpn. J. Appl. Phys.*, vol. 36, pp. 1335-1340 (Mar. 1997).

Wang et al., "A nanotube-based field-emission flat panel display", *Appl. Phys. Lett.*, vol. 72, No. 2, pp. 2912-2913 (Jun. 1, 1998).

Bonard et al., "Field emission from single-wall carbon nanotube films", *Appl. Phys. Lett.*, vol. 73, No. 7, pp. 918-920 (Aug. 17, 1998).

Thess et al., "Crystalline Ropes of Metallic Carbon Nanotubes", *Science*, vol. 273, pp. 483-487 (Jul. 26, 1996).

Bower et al., "Synthesis and structure of pristine and alkali-metal-intercalated single-walled carbon nanotubes", *Appl. Phys.*, A 67, pp. 47-52 (1998).

Tang et al., "Electronic Stuctures of Single-Walled Carbon Nanotubes Determined by NMR", *Science*, vol. 288, pp. 492-494 (Apr. 21, 2000).

Journet et al., "Large-scale production of single-walled carbon nanotubes by the electric-arc technique," *Nature*, vol. 388, pp. 756-760 (Aug. 21, 1997).

Cassell et al., "Large Scale CVD Synthesis of Single-Walled Carbon Nanotubes," *J. Phys. Chem.* B 103, pp. 6484-6492 (Jul. 20, 1999).

International Search Report for PCT/US05/03991 dated Jun. 22, 2006.

Chinese Office Action for Patent Application No. 01820211.X dated Nov. 18, 2005.

International Search Report for Application No. PCT/US04/02986 dated Jan. 13, 2005.

Supplementary European Search Report for corresponding European Patent No. 03702044.3.

* cited by examiner

COMPUTED TOMOGRAPHY SCANNING SYSTEM AND METHOD USING A FIELD EMISSION X-RAY SOURCE

RELATED APPLICATIONS

This application is a continuation-in-part of U.S. patent application Ser. No. 10/051,183, titled "Large Area Individually Addressable Multi-Beam X-Ray System and Method of Forming Same", filed on Jan. 22, 2002, now U.S. Pat. No. 6,876,724, which is a continuation-in-part of U.S. patent application Ser. No. 09/679,303, titled "X-Ray Generating Mechanism Using Electron Field Emission Cathode", filed on Oct. 6, 2000, now issued as U.S. Pat. No. 6,553,096 on Apr. 22, 2003, each of the above disclosures are incorporated here by reference in their entirety. This application also claims the benefit of U.S. Provisional Patent Application Ser. No. 60/544,420 filed in the United States on Feb. 13, 2004, the entire contents of which are incorporated herein by reference.

STATEMENT REGARDING FEDERALLY SPONSORED RESEARCH OR DEVELOPMENT

At least some aspects of this invention were made with Government support under contract no. N00014-98-1-0597. The Government may have certain rights in this invention.

BACKGROUND

The development of computed tomography (CT) technologies first pioneered by Hounsfield and Cormack were an important breakthrough in the field of radiology. CT scanners are now widely used for diagnostic medical imaging and industrial and security inspection applications. Micro-computed tomography (micro-CT) has recently emerged as a promising non-invasive imaging tool for biomedical research. It has been applied to the high-resolution imaging of bone structures and soft tissues (with the aid of contrast agents) of small animals. The typical design of a micro-CT scanner differs from other CT scanners in that typically the object, rather than the x-ray source, is rotated to collect the projection images for reconstruction. Cone-beam geometry and 2D x-ray detectors are commonly used such that the entire object can be directly reconstructed from a set of recorded 2D images.

The spatial resolution of the micro-CT scanner depends primarily on the x-ray focal spot size, the resolution of the detector, and the scanner geometry. The temporal resolution is determined by the x-ray exposure time and data collection speed of the detector. Although there have been significant innovations and improvements in the x-ray detection technology and imaging algorithms, the basic mechanism of generating x-ray radiation has remained the same. The limitations of the current micro-CT scanners, and to a large extent other CT systems, result primarily to the limitations of their x-ray sources.

Commercial x-ray sources typically use thermionic cathodes to generate the electrons used to produce x-ray radiation. The thermal process used in such devices has several inherent limitations including high operating temperature, slow response time, and the production of electrons having a random spatial distribution. The high operating temperature can result in a short cathode lifetime due to breakage of the cathode filament, and x-ray tubes requiring a large size. To provide the small focal spot size required for high spatial resolution, complicated electron optics are employed. As a result, micro-focus x-ray tubes are typically bulky, costly and have limited lifetime.

In addition to requiring high operating temperatures, thermionic emission is inherently a relatively slow emission process. Conventional x-ray tubes rely on mechanical shutters to switch on and off the x-ray exposure, which can result in slow response times. Grid-controlled x-ray tubes have been developed that provide improved response time and short x-ray pulse width, but the temporal resolution of such tubes is still limited and the x-ray waveform can not be easily programmed. The low temporal resolution and the large number of projection images required for reconstruction have prevented dynamic CT imaging of moving objects such as hearts which are important for diagnosis of coronary artery disease.

Although "ultra-fast" CT scanners such as the Dynamic Spatial Reconstructor and the electron-beam CT (EBCT) scanner with scanning time of less than 100 msec have been developed for such purposes, these systems can be much larger that other CT systems, limiting their availability for use. Recent research has shown that it is also possible to obtain dynamic information using conventional CT with spiral capability and fast rotation speed with electrocardiograph (ECG) triggering. But dynamic cardiac CT imaging has not been demonstrated using micro-CT scanners.

Electron field emission is a quantum process where under a sufficiently high external electrical field electrons can escape from the metal surface to the vacuum level by tunneling. Electron field emission is preferred to thermionic emission, as heating is not required and the emission current can be controlled by the external field to give instantaneous response time. In addition field emitted electrons are confined to a narrow cone angle along the electrical field direction, whereas thermal electrons can be spatially randomly distributed. The basic physics of field emission is summarized by the Fowler-Nordheim equation, $$I = \alpha V^2 \exp(-b\phi^{3/2}/\beta V) \tag{1}$$

which states that the emission current (I) increases exponentially with increasing voltage (V). For a metal with a flat surface, the threshold field required for electron emission is typically around $10^4 V/\mu m$, which is impractically high. Consequently, electron field emitters rely on field enhancement ($\beta$) at sharp tips or protrusions of the emitter. One way to fabricate sharp tipped field emitters is by a lithography process. Such emitters, called Spindt tip emitters, have not been used in practical devices because of low emission current, poor stability, and high cost.

X-ray tubes using field emission cathodes have been investigated in the past. In the early systems, metal tips were used as the cathodes. Electrons were extracted by applying a pulsed high voltage between the target and cathode using Max generators, which use a series of discharging capacitors to generate the required threshold field. X-ray radiation is generated when the field emitted electrons bombard on target. The advantages of field emission x-ray tubes as compared to thermionic x-ray tubes in terms of their resolution and required exposure time have been demonstrated in clinical studies. The metal-tip emitters of these early systems were shown to be inefficient. The x-ray tubes were shown to have a limited lifetime of about 200 to 300 exposures, and exhibited slow repetition rates. In addition, with the diode configuration of the tubes, the acceleration voltage and the tube current could not be independently controlled. Field emission x-ray tubes using other types of emitters, such as the Spindt tips described above and diamond emitters, have also been investigated. The highest electron current demonstrated in these x-ray tubes has only been on the order of micro amps.

The carbon nanotube (CNT) is a relatively new carbon allotrope discovered about a decade ago. A CNT includes either a single graphene shell, referred to as a single-walled carbon nanotube (SWNT), or multiple concentric graphene shells, referred to as multi-walled carbon nanotube (MWNT). CNTs are typically about 1–50 nm in diameter and 1–10 μm in length. Considerable progress has been made recently in the fabrication of CNTs with controlled structure and morphology. Technologies have been developed for assembly and integration of CNTs into device structures.

Research has shown that CNTs are promising electron field emitters. The atomically sharp tips and large aspect ratios (typically >$10^3$) of CNTs provide for large field enhancement factors ($\beta$), thus requiring lower threshold fields for emission than other types of emitters such as the Spindt tips. In addition, the field emitted electrons have been shown to have an energy spread of ~0.5 eV and a spatial divergence angle in a direction parallel to the electrical field of less than 5° degree half angle. CNT emitters have been shown to be stable at high currents. For example, a stable emission current of >1 μA (>$10^6$ A/cm$^2$ density) has been observed from an individual SWNT. Macroscopic cathodes have been demonstrated to emit stable emissions of over 200 mA from a 3 mm diameter sample under DC operating conditions, and a peak emission current of 3000 A from a 9 cm cathode at 1 μs pulse width at 200 KV anode voltage. These properties make the CNT emitters attractive for various device applications. For example, field emission flat panel displays (FEDs), lighting elements, and discharge tubes for over-voltage protection have been demonstrated having CNT-based "cold" cathode emitters.

SUMMARY

Accordingly, a method and system are disclosed for computed tomography scanning system and method using a field emission x-ray source.

An exemplary micro computed tomography scanner comprises a micro-focus field emission x-ray source, an x-ray detector, an object stage placed between the x-ray source and the detector, an electronic control system and a computer that control the x-ray radiation and detector data collection, and computer software that reconstructs the three dimension image of the object using a series of projection images collected from different projection angles.

An exemplary method to obtain a computed tomography image of an object in oscillatory motion using the micro computed tomography scanner comprises at least the following steps: the control program reading the position of the object in oscillatory motion from a readout device, the control program activating the field emission x-ray source by sending a pulse voltage applied between the gate electrode and the cathode of the x-ray tube and by sending a signal to the x-ray detector when the object reaches a predetermined position, the field emission x-ray source producing a pulsed x-ray radiation with a predetermined pulse width defined by the width of the pulse voltage applied, the x-ray detector being activated for a fixed dwell time to collect the transmission image of the object formed by the said x-ray pulse, the x-ray source and detector then being switched off, the control program sending a signal to the object stage to rotate the object by a predetermined angular increment, repeating at least one of the above steps until a number of transmission images are collected from different viewing angles with the object in the same position in different periods of the motion, and reconstructing the computed tomography image of the object using the collected projection images.

BRIEF DESCRIPTION OF THE DRAWINGS

The accompanying drawings provide visual representations which will be used to more fully describe the representative embodiments disclosed here and can be used by those skilled in the art to better understand them and their inherent advantages. In these drawings, like reference numerals identify corresponding elements, and.

DETAILED DESCRIPTION

Figure 1:
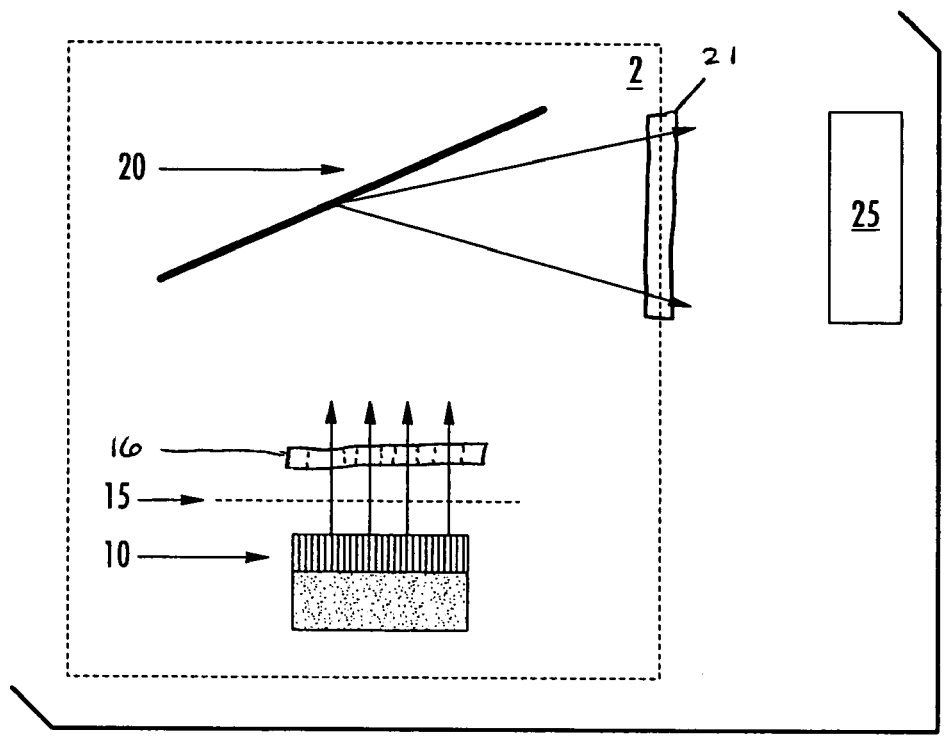
FIG. 1 illustrates an arrangement for measuring the focal spot size of an x-ray tube.

Various aspects will now be described in connection with exemplary embodiments, including certain aspects described in terms of sequences of actions that can be performed by elements of a computer system. For example, it will be recognized that in each of the embodiments, the various actions can be performed by specialized circuits or circuitry (e.g., discrete and/or integrated logic gates interconnected to perform a specialized function), by program instructions being executed by one or more processors, or by a combination of both.

Thus, the various aspects can be embodied in many different forms, and all such forms are contemplated to be within the scope of what is described. For each of the various aspects, any such form of embodiment can be referred to here as "logic configured to" perform, or "logic that" performs a described action.

CNT-based field emission x-ray sources capable of producing sufficient flux for imaging human extremities are described in U.S. patent application Ser. Nos. 09/679,303 and 10/051,183. These field-emission x-ray tube sources include a triode-type structure with a CNT cathode, a gate electrode, and a metal target housed in a vacuum tube with a Be window. The electrons are extracted from the cathode by applying a gate voltage $V_g$ between the cathode and gate, which are then accelerated by a high voltage $V_a$ between the gate and the target. The tube current and the acceleration voltage can be independently controlled. By replacing the DC gate voltage with an amplified signal from a function generator, electron emission and thus x-ray radiation having programmable waveform can be produced.

X-ray tubes having such designs can have the following characteristics:

Tube current: 200 mA from a 3 mm-diameter cathode;
Acceleration voltage: stable emission and x-ray generation at 60 KVp and pulsed emission at 200 KV;
Pulsation: pulsed x-ray radiation with a pulse width less than 10 μs; pulsed emission of 1 μs width with sharp current onset, showing a one-to-one correspondence between the control signal and the output x-ray;

Focal spot: a focal spot size about the same as the cathode-size at 2 cm anode-cathode distance under the triode-mode without any focusing electrode; capability of generating sufficient flux for small animal imaging at 100 μm effective focal spot size; and Imaging: sufficient x-ray flux to image human extremities.

These results demonstrate that a micro-focus x-ray source based on the field emission mechanism can offer advantages in several areas compared to thermionic emission micro-focus x-ray sources. These areas include:

Temporal resolution: the use of the field emission cathode enables instantaneous response time and narrow x-ray pulse width; 10 μsec pulse widths are attainable with 1 μsec rising/falling time; both the pulse width and the repetition rate can be readily programmed;

Spatial resolution: the narrow intrinsic divergence of the field-emitted electrons (<2°) allows for a high spatial resolution; 100 μm resolution achievable without any focusing electrodes; 10–30 μm spatial resolution achievable as described below; fabrication of multiple cathodes capable of being electronically switched allowing x-ray sources with variable effective focal spot size;

Life time: thermionic cathode field emitters can extend the lifetime of the x-ray tube;

Flux: the maximum x-ray photon flux that can be obtained at a certain spatial resolution in other x-ray tubes is determined primarily by how fast heat can be dissipated from the anode—thus, by operating in the pulse mode with a significantly reduced pulse width and by synchronizing x-ray exposure with data collection such that the electron beam is on only when the image is collected, the head load on the anode can be significantly reduced, resulting in a higher flux at a given focal spot size compared to other x-ray tube designs; and Size: because of the low operating temperature of the field emission cathode (e.g., 300K) and the ease of focusing, the size of the x-ray tube can be substantially smaller that other x-ray tube designs.

Results show that the micro-CT described here can be used for dynamic cardiac and pulmonary imaging of small animals which can not be easily obtained using other micro-CT scanners. Compared to commercially available micro-CT scanners, advantages of this system include:

high temporal resolution;

capability of synchronizing x-ray exposure with data collection, objection rotation, and motion;

low x-ray dosage; and high resolution at reduced cost and size.

In addition, these commercially available micro-CT scanners typically use cone beam geometry and flat panel area detectors. A typical CMOS area detector can capture data at the maximum rate of 50 frames/second. Typical grid-controlled x-ray tubes operate at ~100 ms pulse widths. Thus, it can be difficult to obtain dynamic cardiac CT images of small animals, such as mice, because during one exposure, the cardiac motion could undergo a full cycle of motion.

Using a system such as that described here, 10 μs x-ray pulses having rising/falling times of 1 μs are possible. Moreover, the described system can produce a field emission x-ray with 100 μm resolution that is, in turn, capable of generating CT-quality projection images of a mouse at 10 msec per frame at 45 kVp. The system x-ray source can deliver up to 1 mA anode current, enabling 1–10 msec per frame at 30 μm resolution. By combining ECG-gated triggering and the CMOS 2D x-ray detector, dynamic imaging of a full cycle of cardiac motion can be achieved in about 10 minutes.

Micro-focus Field Emission X-Ray Source

According to an exemplary embodiment, a triode-type field-emission x-ray tube is described having a CNT-based electron field emission cathode in a dynamic vacuum chamber. FIG. 1 shows a schematic representation of an x-ray tube or source 2 comprising CNT cathodes 10, an electron gate 15 and a metal anode target 20 with an optional cooling mechanism. In exemplary embodiments, the x-ray tube includes a 1 mm diameter CNT cathode, an electron extraction gate, and a Mo target with 6° take-off angle in the reflection mode. The gate electrode is 150 μm away from the cathode. Gate voltage in the tube is controlled by a 0–60 KV power supply. Current stability can be monitored in the system using software, e.g., using Labview (National Instruments) software. The vacuum chamber is pumped to less than 10–7 Torr. The vacuum chamber may include an x-ray transparent window 4 for passing the x-rays from target 20. Performance characteristics of this x-ray tube are summarized below. X-ray source 2 may include an electron focusing electrode 16 for focusing electrons emitted by cathodes 10. X-ray source 2 may include an x-ray transparent window 21.

In one embodiment, cathodes 10 can have different emission areas with different emission rates. At any given time, only one field emission cathode emits electrons. A spatial resolution of x-ray source 2 can be changed by selecting a field emission cathode with a different emission area. The cathode is selected with a large emission area for low-resolution and high x-ray flux purpose. The cathode is selected with a small area for high resolution imaging.

Resolution

The field emitted electrons from the CNT cathode have a very small divergent angle. In the triode-configuration, there is a one-to-one correspondence between the cathode size and target area bombarded by the electrons without any focusing. This is attributed to the very small intrinsic divergence angle of the field emitted electrons which is an advantage of the field-emission x-ray tubes.

The focal spot size of the above x-ray tube was measured using radiographs of a thin tungsten wire following the method described by the European Standard EN 12543-5. A fine W wire of known diameter was placed between the x-ray source and the detector, such as between source 2 and detector 25 shown in FIG. 1. The profiles of the x-ray beam after passing the W wire were collected with the wire in two orthogonal directions and were analyzed to obtain the effective focal spot size of the source. For a CNT-based cathode without a focusing cap, the measured focal spot size is 0.77 mm and 0.10 mm for the horizontal and vertical directions, respectively.

Energy Spectrum

Figure 2:
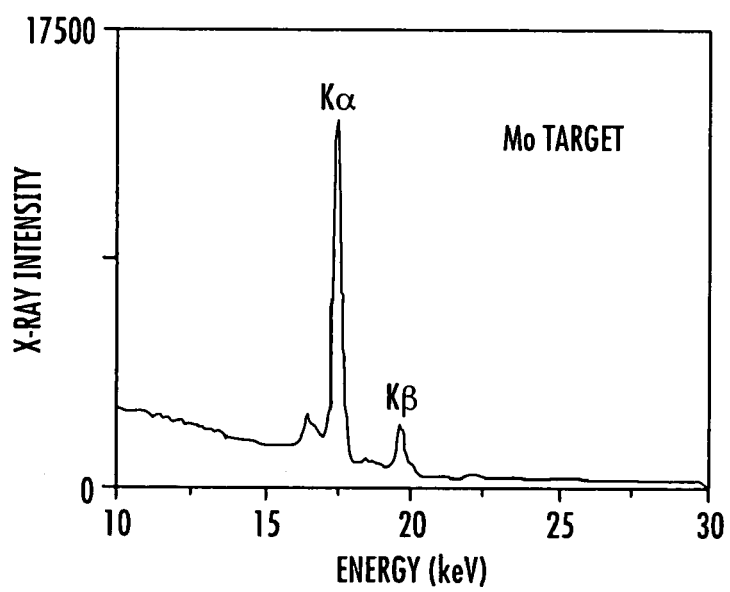
FIG. 2 illustrates energy spectrum measurements for a molybdenum target without filtering at 40 kV.

Energy spectrum measurements for a molybdenum target without filtering at 40 kV are shown in FIG. 2. The spectra were recorded using a Si-PIN photodiode detector (a model with up to 30 KV energy) placed outside the x-ray chamber. The results were similar to that from other sources. In one embodiment, detector 25 of x-ray source 2 may include at least one filter for absorbing x-ray photons within a predetermined energy range.

Tube Current (Flux)

The maximum emission current density that can be achieved depends on several factors, including the total emission area, current, and the lifetime and pulse width required. In general, a higher current density can be achieved from a smaller cathode because sample uniformity becomes less of a contributing factor. This can aid in the performance of a micro-focus x-ray system such as that described here. The system described here demonstrated a stable emission at 6 mA from a 1 mm diameter cathode (750 mA/cm$^2$) at 40 KVp anode. This remains far below the theoretical limit of emission from CNTs. For example, experiments have been shown to produce 1 μs-width, 3000 Ampere current from a 9 cm diameter cathode at 220 KVp, albeit at a much reduced life-time.

High Voltage Stability

Due to hardware limitations, the maximum operating voltage of the current testing system used to characterize the described device is limited to 60 KVp anode voltage. Under these conditions, the emission current remains stable. No ion-sputtering related damage was observed. Measurements conducted at other facilities have demonstrated electron emission at 220 KVp anode voltage in the diode configuration with the described device.

Micro-Ct Scanner Using the Field Emission Micro-focus X-Ray Source

Figure 3:
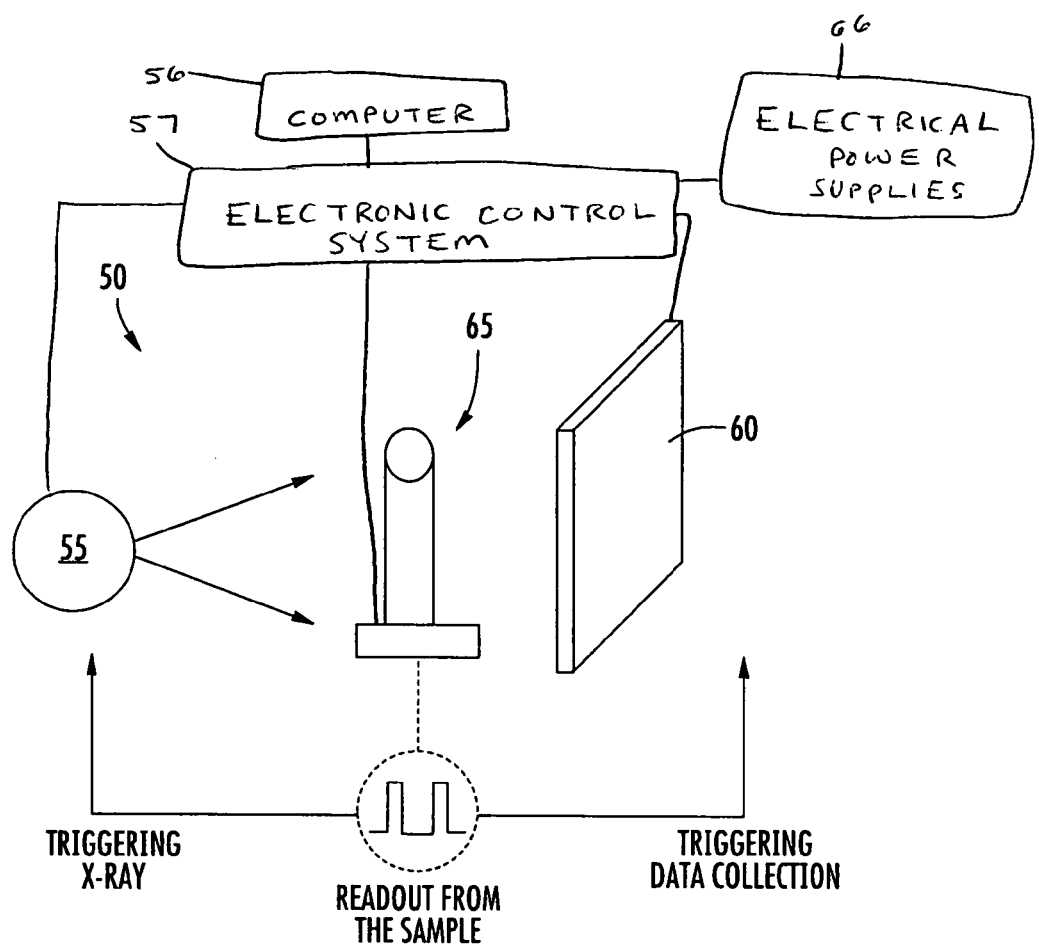
FIG. 3 illustrates a micro-CT scanner system according to an exemplary embodiment.
Figure 4A:
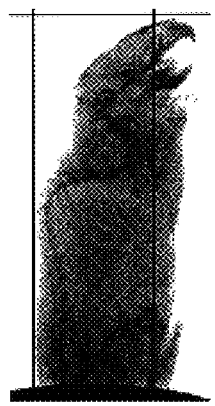
FIGS. 4A to 4E illustrate the imaging of a normal C57BL/6 strain, eight-week-old mouse carcass, using the micro-CT scanner system shown in FIG. 3.
Figure 4B:
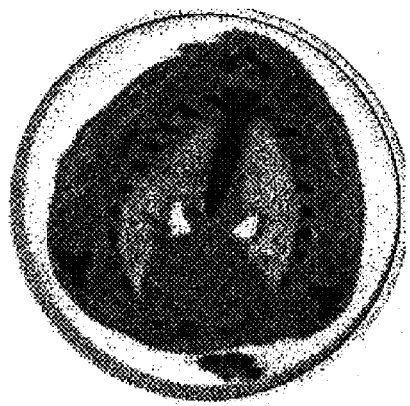
Figure 4C:
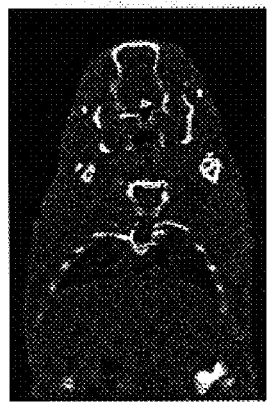
Figure 4D:
Figure 4E:
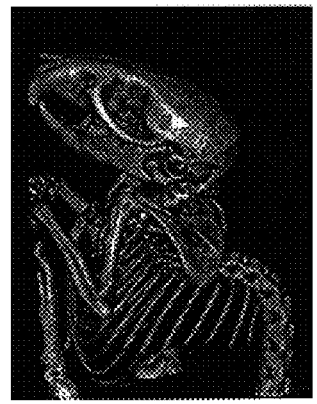

FIG. 3 shows a micro-CT scanner system 50 according to another exemplary embodiment that includes a field-emission micro-focus x-ray tube/source 55, such as the x-ray source described above in connection with FIG. 1. The system 50 includes a detector 60 such as a flat panel digital X-ray image sensor (e.g., Hamamatsu C7921) with a CsI scintillation plate. A 1056×1056 photodiode array at 50×50 μm pixel resolution can be placed behind the object to measure the transmitted x-ray intensity. The video output can be a 12-bit digital signal with a bandwidth of 6.25 MHz. When running in a 4×4 binning mode, the system can be capable of delivering a frame rate of 16 frames-per-second (fps) at 258×258 pixels per frame. The sensor can be externally triggered using a transistor-transistor logic (TTL) signal, such that the frame speed can be the same as the frequency of the triggering signal. The sensor can be connected to a personal computer (PC) 56 via an image acquisition board (e.g., National Instrument PCI-1422), which can capture up to 16 bits wide data at a clock speeds of up to 40 MHz. A high precision optical rotation stage attached to a stepper motor control system can be used as the sample stage 65. For example, a Velmex (Bloomfield, N.Y.) VXM stepper motor controller can be attached to the control computer through its serial port. Rotational accuracy is estimated to be better than 0.10 degrees. Stage 65 may be configured to detect the motion of an object under imaging and can output a signal related to the position of the object under imaging. Computer 56 may interface with x-ray tube/source 55, detector 60, and sample stage 65 by using an electronic control system 57. Computer 56 and electronic control system 57 may be configured to control x-ray radiation and detector data collection. Further, computer 56 and electronic control system 57 can be configured to select x-ray photons within a predetermined energy range. Electrical power supplies 66 may supply power for system 50. X-ray tube/source 55 may have a spatial resolution better than 1 micron.

Programs for controlling the entire operation of the micro-CT scanner can be written using any suitable control language program, such as Labview. These programs can control system parameters such as the gate voltage, acceleration voltage, exposure time, pulse rate, rotation stage, and data readout. Moreover, an image reconstruction method, such as Feldkamp's method, can be implemented for reconstructing the acquired images. The described field emission micro-CT scanner of FIG. 3 has demonstrated a capability of CT imaging small animals, dynamic imaging, and trigger and gated imaging. Representative imaging results obtained using this micro-CT system are discussed below.

Small Animal Imaging

FIGS. 4A to 4E illustrates the imaging of a normal C57BL/6 strain, eight-week-old mouse carcass, using an exemplary micro-CT scanner system, such as the system 50 shown in FIG. 3. The scanning parameters are as follows: gate voltage=1 kV; tube voltage=40 kVp; tube emission current=0.12 mA; exposure time=1 sec/frame for 600 frames across 360°; and a source-to-detector distance of about 20 cm. A modified Feldkamp reconstruction method was used for reconstructing the tomographic images shown in FIG. 4 for three different orientations. In addition, results obtained from surface rendering of the bony structures are also shown. These images represent what are believed to be the first of such reported CT images using field-emission x-ray source. The figure clearly shows the anatomical details of the mouse, demonstrating the ability to obtain CT images using a CNT-based micro-CT scanner, such as that shown in FIG. 3, and a functional configuration of a system for providing small animal imaging.

Dynamic Imaging

Figure 5A:
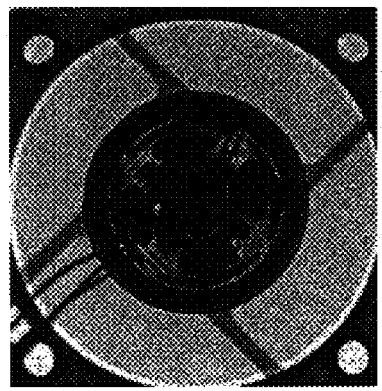
FIGS. 5A to 5D illustrate the dynamic imaging of a computer cooling fan rotating at approximately 1000 RPM using the system shown in FIG. 3.
Figure 5B:
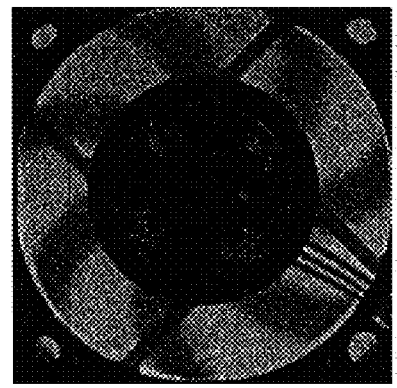

To demonstrate the dynamic imaging capability of the system, a computer cooling fan rotating at ~1000 RPM was imaged using the system shown in FIG. 3. FIGS. 5A to 5D show the results of the imaging taken under two different conditions: FIG. 5A) an image sensor at 16 fpd under continuous x-ray exposure, which represents a typical imaging condition; and FIG. 5B) imaging with the x-ray repetition rate (f), pulse width, and delay $T_d$ of 14 Hz, 1 msec, and 64 msec, respectively. Under the condition in FIG. 5A), the individual blades were not resolved, as was expected. Under the condition in FIG. 5B), the individual blades were clearly resolved. The sharpness of the image can depend on a ratio of the x-ray pulse width to the blade rotation speed. The image becomes blurred when the motion of the object within the duration of the x-ray exposure is non-negligible.

Figure 5C:
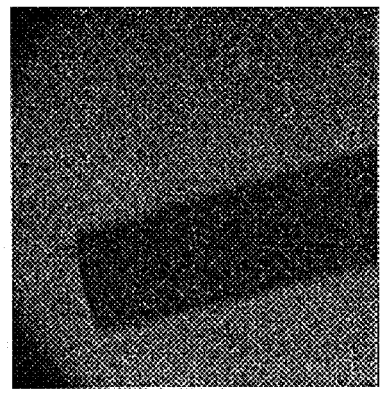
Figure 5D:
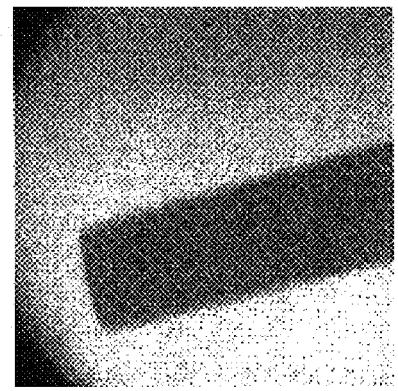

Gated imaging can be readily achieved in the current system with the field-emission x-ray source and the digital imaging sensor which enables time-resolved studies, such as cardiovascular dynamics. In addition multiple exposures can be accumulated to increase the signal-to-noise ratio. This capability was demonstrated using a rotating blade of fan. As shown in FIG. 5, the object being imaged is a fan blade rotating at a speed of about 100 RPM. The position of the blade is a sine function of time. The individual frames were taken by a 2 msec long x-ray pulse @ 14 Hz. FIG. 5C is a single frame image of the fan blade; FIG. 5D is the sum of 20 frames triggered for the same phase of the motion obtained from 20 consecutive periods. Compared to a single frame, the image signal strength in FIG. 5D is increased significantly. This can allow for an extension of the exposure time without blurring the images of a moving object. Thus, if a physiological signal is used as the trigger, such as the electrocardiograph, the system can be used to perform numerous important medical imaging tasks.

The executable instructions of a computer program for controlling the system shown in FIG. 3 can be embodied in any computer readable medium for use by or in connection with an instruction execution system, apparatus, or device, such as a computer based system, processor containing system, or other system that can fetch the instructions from the instruction execution system, apparatus, or device and execute the instructions.

As used here, a "computer readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium, such as a removable storage device. More specific examples (a non exhaustive list) of the computer readable medium can include the following: an electrical connection having one or more wires, a portable computer diskette, a random access memory (RAM), a read only memory (ROM), an erasable programmable read only memory (EPROM or Flash memory), an optical fiber, and a portable compact disc read only memory (CDROM).

It will be appreciated by those of ordinary skill in the art that the concepts and techniques described here can be embodied in various specific forms without departing from the essential characteristics thereof. The presently disclosed embodiments are considered in all respects to be illustrative and not restrictive. The scope of the invention is indicated by the appended claims, rather than the foregoing description, and all changes that come within the meaning and range of equivalence thereof are intended to be embraced.

What is claimed is:

1. A micro computed tomography scanner, comprising:
   a micro-focus field emission x-ray source comprising addressable nanostructure-containing electron field emission materials, a gate electrode and a metal anode, wherein voltage is applied between the gate electrode and the electron field emission materials to generate an electron beam to bombard the metal anode with electrons for generating x-ray radiation;
   an x-ray detector configured to collect a projection image of an object formed by the x-ray radiation;
   an object stage placed between the x-ray source and the detector for positioning the object in a plurality of predetermined positions with respect to the x-ray radiation;
   an electronic control system and a computer that control generation of the x-ray radiation by the x-ray source and collection of a plurality of projection images from different projection angles by the x-ray detector; and
   whereby the micro computer tomograghy scanner is configured for generating a three dimensional image of the object using the plurality of projection images collected from the different projection angles, wherein application of a voltage between the gate electrode and the electron field emission materials and positioning of the object in the predetermined positions are coordinated such that the plurality of projection images are collected by the x-ray detector.

2. The scanner of claim 1, wherein the micro-focus field emission x-ray source comprises:
   an electron field emission cathode;
   an x-ray transparent window;
   a vacuum enclosure; and
   electrical power supplies;
   wherein the pate electrode comprises an electron extraction gate electrode; and
   wherein the metal anode comprises a cooling mechanism.

3. The scanner of claim 2, wherein electrons are emitted from the cathode when an electrical field between the cathode and the extraction gate cathode exceeds a critical value, and the x-ray radiation is generated when the emitted electrons are accelerated by an acceleration voltage applied between the gate electrode and the metal anode and bombard on the metal anode.

4. The scanner of claim 1 wherein the micro-focus field emission x-ray source comprises:
   at least one electron focusing electrode.

5. The scanner of claim 1, wherein the micro-focus field emission x-ray source comprises:
   multiple field emission cathodes with different emission rates, wherein at any given time only one field emission cathode emits electrons, a spatial resolution of the x-ray source can be changed by selecting a field emission cathode with different emission area, wherein the cathode is selected with a large emission area for low-resolution and high x-ray flux purpose, and wherein the cathode is selected with a small area for high resolution imaging.

6. The scanner of claim 1, comprising:
   at least one filter used to absorb x-ray photons within a predetermined energy range.

7. The scanner of claim 1, comprising:
   wherein the electronic control system and the computer are configured to select x-ray photons within a predetermined energy range.

8. The scanner of claim 1, wherein the x-ray detector is a two-dimensional detector.

9. The scanner of claim 1, wherein the x-ray source is stationary and the object stage can rotate about a center of rotation during measurement.

10. The scanner of claim 1, wherein at least one of the x-ray source and the detector can rotate around the object stage during measurement.

11. The scanner of claim 1, wherein the micro-focus field emission x-ray source includes a cathode comprising at least one of the carbon-based nanotubes, non-carbon based nanotubes, and nanowires.

12. The scanner of claim 1, wherein the micro-focus field emission x-ray source includes a cathode containing carbon nanotube-containing electron field emission materials.

13. The scanner of claim 1, wherein the micro-focus field is operable to produce an x-ray flux selected by selecting an electrical field between the gate electrode and the cathode, and wherein an energy of an x-ray photon is selected by selecting of an electrical field between the anode and the gate electrode.

14. The scanner of claim 1, wherein the micro-focus field emission x-ray source generates x-ray radiation with at least one of cone-beam, fan-beam or pencil-beam geometry.

15. The scanner of claim 1, wherein the micro-focus field emission x-ray source is operable to generate x-ray radiation with a spatial resolution better than 100 microns.

16. The scanner of claim 1, wherein the micro-focus field emission x-ray source is operable to generate x-ray radiation with a spatial resolution better than 50 microns.

17. The scanner of claim 1, wherein the micro-focus field emission x-ray source is operable to generate x-ray radiation with a spatial resolution better than 30 microns.

18. The scanner of claim 1, wherein the micro-focus field emission x-ray source is operable to generate x-ray radiation with a spatial resolution better than 10 microns.

19. The scanner of claim 1, wherein the micro-focus field emission x-ray source is operable to generate x-ray radiation with a spatial resolution better than 1 micron.

20. The scanner of claim 1, wherein pulsed x-ray radiation is generated by applying a pulsed voltage between the gate electrode and the cathode while an acceleration voltage is kept constant, and wherein the x-ray source is operable to generate plused x-ray radiation having an x-ray pulse-width and repetition rate programmable by programming the pulsed voltage, and a one-to-one relation exists between the pulsed voltage applied and the pulsed x-ray generated.

21. The scanner of claim 20, wherein the x-ray pulse width can be narrower than 1 microsecond and the pulse rising and falling time can be shorter than 0.2 microsecond.

22. The scanner of claim 1, wherein the scanner is configured to compute a tomography image of an object by at least one of the steps of:
    sending a signal to the object stage to rotate the object by a predetermined angular increment;
    sending signals to the x-ray source and the detector to initiate x-ray radiation and data acquisition after the object is placed in position on the object stage;
    a pulsed voltage being applied between the gate electrode and a cathode of the field emission x-ray tube such that a pulsed x-ray radiation with a fixed pulse width is generated;
    the detector being activated to collect the image of the object formed by the x-ray radiation at a particular projection angle and the data being transferred to the computer;
    after x-ray exposure and data collection, repeating at least one of the above steps until sufficient numbers of projection images are collected; and
    computing the computed tomography images of the object using the collected projection images.

23. The scanner of claim 1, wherein the scanner obtains dynamic computer tomography images of the object,
    wherein the object stage is configured to detect the motion of the object under imaging and to output a signal that is related to the position of the object under imaging.

24. A method to obtain a computed tomography image of an object in oscillatory motion using the device of claim 23, the method comprising at least the following steps:
    a control program reading the position of the object in oscillatory motion from a readout device;
    the control program activating the field emission x-ray source by sending a pulse voltage applied between a gate electrode and a cathode of the x-ray source and by sending a signal to the x-ray detector when the object reaches a predetermined position;
    the field emission x-ray source producing a pulsed x-ray radiation with a predetermined pulse width defined by the width of the pulse voltage applied;
    the x-ray detector being activated for a fixed dwell time to collect the transmission image of the object formed by the said x-ray pulse;
    the x-ray source and detector then being switched off;
    the control program sending a signal to the object stage to rotate the object by a predetermined angular increment;
    repeating at least one of the above steps until a number of transmission images are collected from different viewing angles with the object in the same position in different periods of the motion; and
    reconstructing the computed tomography image of the object using the collected projection images.

25. The method of claim 24, wherein the object under imaging is a cardiac motion of a small animal, and the readout device reads an EGG signal of the small animal.

26. The method of claim 24, wherein the object is the respiratory system of a small animal.

\* \* \* \* \*